United States Patent [19]

Golborn et al.

[11] 3,959,551

[45] May 25, 1976

[54] DIALKYL ALKYL AND AROMATIC SULFONAMIDOMETHYL PHOSPHONATES

[75] Inventors: Peter Golborn, Lewiston; James J. Duffy, Buffalo, both of N.Y.

[73] Assignee: Hooker Chemicals & Plastics Corporation, Niagara Falls, N.Y.

[22] Filed: Dec. 31, 1974

[21] Appl. No.: 537,721

Related U.S. Application Data

[62] Division of Ser. No. 239,757, March 30, 1972, Pat. No. 3,870,771.

[52] U.S. Cl. .............................. 428/272; 260/944; 260/947; 428/276; 428/921
[51] Int. Cl.² ............................................ C07F 9/40
[58] Field of Search .................. 428/272, 276, 921; 260/944, 947

[56] References Cited
UNITED STATES PATENTS 3,870,771  3/1975  Golborn .............................. 260/944

Primary Examiner—Marion E. McCamish
Attorney, Agent, or Firm—Peter F. Casella; William J. Crossetta, Jr.

[57] ABSTRACT

New compounds are disclosed of the formula:

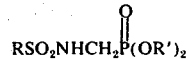

wherein R is selected from the group consisting of lower alkyl of 1–6 carbon atoms, phenyl and alkyl substituted phenyl and R' is selected from the group consisting of phenyl, lower alkenyl and halogen substituted and unsubstituted lower alkyl of 1–6 carbon atoms. The compounds of this invention are useful as flame retarding agents for textile materials and in the production of polymers and copolymers which possess flame retardant properties.

56 Claims, No Drawings

DIALKYL ALKYL AND AROMATIC SULFONAMIDOMETHYL PHOSPHONATES

This is a division of application Ser. No. 239,757, filed Mar. 30, 1972, now U.S. Pat. No. 3,870,771.

FIELD OF INVENTION

This invention relates to novel compounds of the formula

wherein R is selected from the group consisting of lower alkyl of 1–6 carbon atoms, phenyl and alkyl substituted phenyl and R' is selected from the group consisting of phenyl, lower alkenyl and halogen substituted and unsubstituted lower alkyl of 1–6 carbon atoms. The invention includes methods of applying the above novel compounds to normally flammable textiles and thermoplastic or thermosetting resin compositions so as to render them flame retardant.

BACKGROUND OF THE INVENTION

Many flame retarding agents and methods of application have been developed in attempts to obtain flame resistant textile materials and thermoplastic or thermosetting resin compositions.

Flame retardant textiles have been produced by depositing metal oxides, within or on the textile fibers, by the successive precipitation of ferric oxides and a mixture of tungstic acid and stannic oxide or by successive deposition of antimony trioxide and titanium dioxide. Such processes require plural treatment baths in which strongly acidic solutions are employed thus posing the problem of possible textile degradation. Furthermore, metal oxide coatings on textile materials create difficulties in subsequent dyeing processes which deleteriously affect the hand of the finished product. Another process involves the use of a single processing bath wherein a dispersion of a chlorinated hydrocarbon and finely divided antimony oxide is padded on the textile material. Near the textile combustion temperatures antimony oxide will react with hydrogen chloride, generated by degradation of the chlorinated hydrocarbon, to form antimony oxychloride which acts to suppress flame. This combination of a chlorinated hydrocarbon and finely divided antimony oxide are not acceptable finishes for closely woven textiles as they deleteriously affect the hand of the finished product. A further process for imparting flame resistance to cellulosic materials is by the esterification of the cellulose with diammonium hydrogen orthophosphate. Textile products so treated however are subjected to metathesis reaction with cations during washing, and must be regenerated by reacting the wash product with an ammonium chloride solution.

The product of thermoplastic resin compositions which are flame retardant is of considerable commercial importance. For example, such articles as castings, moldings, foamed or laminated structures and the like are required, or are at least desired, to be resistant to fire and flame and to possess the ability to endure heat without deterioration. The use of various materials incorporated into thermoplastic resins so as to improve the flame retardancy thereof has been known. Many compounds have been commercially available for such use, among them being chlorostyrene copolymers, chlorinated paraffin wax in admixture with triphenyl styrene, chlorinated paraffins and aliphatic antimonical compounds, as well as antimony oxide — chlorinated hydrocarbon mixtures. A problem associated with these compounds has been however, the fact that generally a large amount, i.e. upwards of 35% of additive, must be incorporated into the resin in order to make it sufficiently flame retardant. Such large amounts of additive may deleteriously affect the physical characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out of the resin after incorporation therein.

OBJECTS OF THE INVENTION

It is, therefore, a principal object of this invention to provide novel compounds of the formula:

wherein R is selected from the group consisting of lower alkyl of 1–6 carbon atoms, phenyl and alkyl substituted phenyl and R' is selected from the group consisting of phenyl, lower alkenyl and halogen substituted and unsubstituted lower alkyl of 1–6 carbon atoms.

It is also an object of this invention to provide flame retarding textile materials comprising normally flammable cellulosic, proteinaceous or blends thereof. Another object is to provide a method for treating normally flammable cellulosic, proteinaceous or blends thereof to render them flame retardant. Another object is to provide flame retarding thermoplastic or thermosetting resin compositions comprising normally flammable thermoplastic or thermosetting resin materials. A further object is to provide a process for treating normally flammable thermoplastic or thermosetting resin compositions to render them flame retardant. A particular object is to devise a composition comprising normally flammable cellulosic, proteinaceous or analogous man-made materials and an effective flame retardant amount of the compound represented by the formula

wherein R and R' are as above described.

A further particular object is to devise a composition comprising normally flammable thermoplastic or thermosetting polymer and an effective flame retarding amount of the before described novel compound.

These and other objects of the present invention will be obvious from the following description.

DESCRIPTION OF THE INVENTION

In accordance with this invention there are provided novel compounds, for imparting flame retardancy to textiles and thermoplastic or thermosetting resin materials, of the formula

wherein R is selected from the group consisting of lower alkyl of 1–6 carbon atoms, phenyl and alkyl substituted phenyl and R' is selected from the group consisting of phenyl, lower allyl and halogen substituted and unsubstituted lower alkenyl 1–6 carbon atoms.

More specifically, the preferred compounds of the present invention include these compounds wherein R and R' are lower alkyl of 1–6 carbon atoms.

Illustrative examples of compounds of the present invention include, for instance, compounds of the general formula such as

   

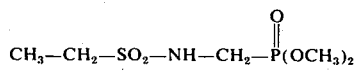   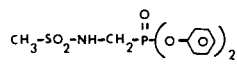

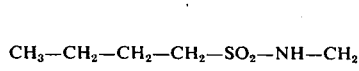   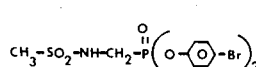

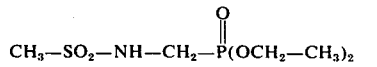   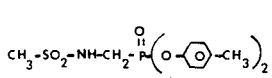

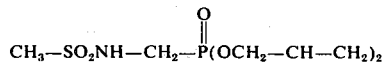   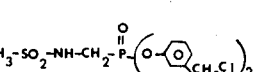

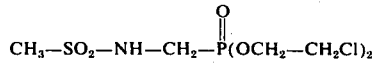   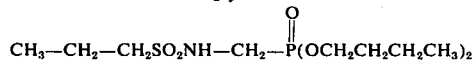

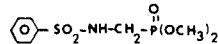   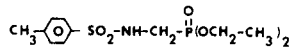

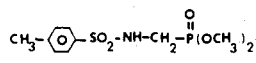   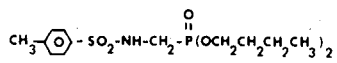

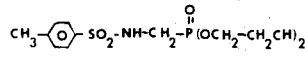   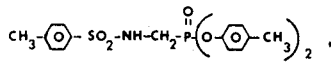

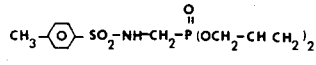   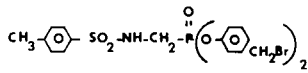

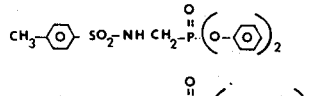   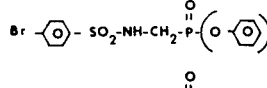

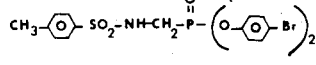   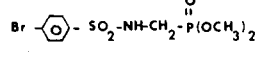

The synthesis of the compositions of the present invention is accomplished by reacting an N-hydroxymethyl sulfonamide of the formula

R SO$_2$NHCH$_2$OH with a trialkyl phosphite of the formula (R'O)$_3$P wherein R and R' are as previously described in a suitable solvent, with an excess of the phosphite, or without solvent. Typically, the reaction is continued for about 1 to about 12 hours. Temperatures are generally about 50°C to about 160°C. Preferably reaction is continued from about 3 to about 6 hours at a temperature of about 80°C to about 120°C. The solvent or other volatiles are thereafter stripped, or otherwise removed from the product. Suitable solvents include benzene, toluene, xylene, the glymes, dimethylformamide and aliphatic or aromatic hydrocarbons. Typical N-hydroxymethyl sulfonamides operable as reactants herein include.

CH$_3$—SO$_2$—NH—CH$_2$—OH
CH$_3$—CH$_2$—CH$_2$—SO$_2$—NH—CH$_2$—OH
CH$_3$—CH$_2$—CH$_2$—CH$_2$—CH$_2$—CH$_2$—SO$_2$—NH—CH$_2$—OH

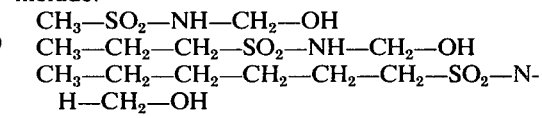

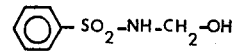

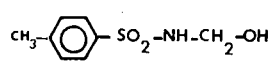

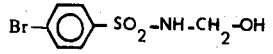

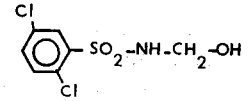

One or more of the novel compounds of this invention may be applied to textile materials by conventional finishing techniques such as by thermal curing so as to incorporate into the textile a flame retardant amount thereof. The compounds of this invention leave advantages over the flame retardant agents of the prior art in that they may be used on a variety of textile materials of different chemical composition, and they may be applied by a variety of methods. They may be applied to materials in either the fiber or fabric form to give flame retarding materials with minimum detectable physical changes in the quality or hand of the textile material.

Cellulosic textile materials may be made flame retardant by way of a variety of methods. Typically, the cellulose products of this invention may be applied to cellulosic materials in several ways to give a durable flame retardant treatment. For example, the product, of this invention may be reacted with formaldehyde to give N-hydroxymethyl derivatives which can react with cellulosic materials in a known manner. Alternatively, aqueous mixtures of the products with formaldehyde, urea, trimethylol melamire or other known cellulose crosslinking agents may be applied to a cellulose substrate with the acid of an acidic catalyst by a pas dry process.

More preferably the H-hydroxynethyl derivative of the products of this invention prepared by the condensation of the products with formaldehyde, are mixed in a aqueous medium with trimethylol melamine and a Lewis acid catalyst such as $NH_4Cl$ or $Zn(NO_3)_2 \cdot 6H_2O$. The cellulosic material is immersed in a aqueous solution of the methylol derivative, trimethylol melamine, and $Zn(HO_3)_2 \cdot 6H_2O$ and squeezed on a two roll padder to 70–90% wet weight pick-up. The material is dried at 220–270°for 1–3 minutes and cured at 300°–370°F for 1–6 minutes in a circulating air oven. The samples are then washed in hot water and dried. The finished samples have a flame retardant add-on of about 5 to about 40% and preferably about 10 to about 25% by weight.

The flame retardant agents of this invention may be applied to various textiles such as cellulosic materials, proteinaceous materials and blends of cellulosic or proteinaceous materials. By cellulosic materials, applicant intends to embrace cotton, rayon, paper, regenerated cellulose and cellulose derivatives which retain a cellulose backbone of at least one hydroxy substituent per repeating glucose unit. By proteinaceous material applicant intends to embrace those textile materials comprising the functional groups of proteins such as the various animal wools, hairs and furs. The flame retardant compounds or additives of the invention may be incorporated into thermoplastic or thermosetting resin compositions by any known method. That is to say, the flame retardant additive may be added to the resin by milling the resin and the additive on, for example, a two-roll mill, or in a Banbury mixer etc., or it may be added by molding or extruding the additive and resin simultaneously, or by merely blending it with the resin in powder form and thereafter forming the desired article. Additionally, the flame-retardant may be added during the resin manufacture, i.e., during the polymerization procedure by which the resin is made, provided the catalysts etc. and other ingredients of the polymerization system are inert thereto. Generally, the compounds of this invention may be incorporated into the thermoplastic on thermosetting resin in flame-retarding amounts, i.e. generally amounts ranging from about 5% by weight, to about 50% by weight, preferably from about 20% by weight, to about 40% by weight, based on the weight of the polymer, have been found sufficient.

The thermoplastic resin embraced within the scope of this invention include the homopolymers and copolymers of unsaturated aliphatic, alicyclic, and aromatic hydrocarbons. Suitable monomers are ethylene, propylene, butene, pentene, hexene, heptene, octene, 2-methylpropene-1, 3-methylbutene-1, 4-methylpentene-1, 4-methylhexene-1,5-methylhexene-1, bicyclo-(2.2.1)-2-heptene, butadiene, pentadiene, hexadiene, isoprene, 2,3-dimethylbutadiene-1,3, 2-methylpentadien- 1,3, 4-vinylcyclohexene, vinylcyclohexene, cyclopentadiene, styrene and methylstylene, and the like.

Other polymers in addition to the above-described olefin polymers that are useful in the invention include polyindene, indenecoumarone resins; polymers of acrylate esters and polymers of methacrylate esters, acrylate and methacrylate resins such as ethyl acrylate, n-butyl methacrylate, isobutyl methacrylate, ethyl methacrylate and methyl methacrylate; alkyd resins and paint vehicles, such as bodied linseed oil; cellulose derivatives such as cellulose acetate, cellulose acetate butyrate, cellulose nitrate, ethyl cellulose, hydroxyethyl cellulose, methyl cellulose and sodium carboxymethyl cellulose; epoxy resins; furan resins (furfuryl alcohol or furfuralketone); hydrocarbon resins from petroleum; isobutylene resins (polyisobutylene); isocyanate resins (polyurethanes); melamine resins such as melamine-formaldehyde and melamine-urea-formaldehyde; oleo-resins; phenolic resins such as phenol-formaldehyde, phenolic-elastomer, phenolic-epoxy, phenolic-polyamide, and phenolic-vinyl acetals; polyamide polymers, such as polyamides, polyamide-epoxy and particularly long chain synthetic polymeric amides containing recurring carbonamide groups as an integral part of the main polymer chain; polyester resins such as unsaturated polyesters of dibasic acids and dihydroxy compounds, and polyester elastomer and resorcinol resins such as resorcinolformaldehyde, resorcinol-furfural, resorcinol-phenol-formaldehyde, resorcinol-polyamide and resorcinol-urea; rubbers such as natural rubber, synthetic polyisoprene, reclaimed rubber, chlorinated rubber polybutadiene, cyclized rubber, butadiene-acrylonitrile rubber, butadiene-styrene rubber, and butyl rubber; neoprene rubber (polychloroprene); polysulfides (Thiokol); terpene resins; urea resins; vinyl resins such as polymers of vinyl acetal, vinyl acetate or vinyl alcohol-acetate copolymer, vinyl alcohol, vinyl chloride, vinyl butyral, vinyl chloride-acetate copolymer, vinyl pyrrolidone and vinylidene chloride copolymers; polyformaldehyde; polyphenylene oxide; polymers of diallyl phthalates and phthalates; polycarbonates of phosgene or thiophosgene and dihydroxy compounds such as bisphenols, phosgene, thermoplastic polymers of bisphenols and epichlorohydrin (trade named Phenoxy polymers); graft copolymers and polymers of unsaturated hydrocarbons and unsaturated monomer, such as graft copolymers of polybutadiene, styrene and acrylonitrile, commonly called ABS resins; ABS polyvinyl chloride polymers, recently introduced under the trade name of Cycovin; and acrylic polyvinyl chloride polymers, known by the trade name Kydex 100.

The polymers of the invention can be in various physical forms, such as shaped articles, for example, moldings, sheets, rods, and the like; fibers, coatings, films and fabrics, and the like.

The compounds of this invention have been found to have particular utility in ABS resins and in elastometric materials such as acrylic rubber; acrylonitrile butadiene styrene terpolymers; butadieneacrylonitrile copolymers; butyl rubber; chlorinated rubbers, e.g., polyvinyl chloride resins, chloroprene rubber, chlorosufonated polyethylene; ethylene polymers, e.g., ethylene-propylene copolymers, ethylene-propylene terpolymers; fluorinated rubbers, butadiene rubbers, e.g., styrene-butadiene rubber, isobutylene polymers, polybutadiene polymers, polyisobutylene rubbers, polyisoprene rubbers; polysulfide rubbers; silicon rubbers; urethane rubbers; high styrene resins latices, high styrene resins, vinyl resins; sponge rubber; and the like.

It should be noted that it is also within the scope of the present invention to incorporate such ingredients as plasticizers, dyes, pigments, stabilizers, antioxidants, antistatic agents and the like to the novel composition.

ASTM Test D2863-70, used in accordance with the following examples, generally provides for the comparison of relative flammability of self-supporting plastics by measuring the minimum concentration of oxygen in a slowly rising mixture of oxygen and nitrogen that will support combustion. The procedure encompasses supporting cylindrical test specimens 70-150 mm in length × 8.0 mm in diameter vertically in a glass tube fitted with controlled upward oxygen/nitrogen gas flow. The top of the specimen is ignited and oxygen flow is adjusted until it reaches that minimum rate at which the specimen is extinguished. before burning 3 minutes or 50 mm whichever happens first. The oxygen index ($n$) is then calculated as follows:

$$n,\% = (100 \times O_2)/(O_2 + N_2)$$

wherein $O_2$ is the volumetric flow of oxygen, at the minimal rate and $N_2$ is the corresponding volumetric flow rate of nitrogen.

A modification of ASTM Test D635-68 used in accordance with the following examples, generally provides for the comparison of burning rates, self-extinguishment and non-burning characteristics of plastics in the form of sheets, bars, plates or panels. The procedure encompasses preparing 150–200 mm × mm cylindrical plastic test samples with an without the subject flame retardant additive. Each sample is marked at points 1 inch and 4 inches from its end and held, marked end in the flame, at a 45° angle in a controlled burner flame (1 inch flame length) for two 30 second attempts. The movement of the flame up the length of the sample through the two points is measured for rate of burning, non-burning or self-extinguishing characteristics. A sample is rated SE (self-extinguishing) if the flame burns through the first point but extinguishes before reaching the second point. A sample is rated NB (non-burning) if, upon ignition it does not burn to the first point.

AATCC test method 34–1969. The vertical Char Test, used in accordance with the following examples, generally provides for the comparison of relative flammability of 2¾ inch × 10 inch fabric test specimens when exposed to a controlled burner flame, under controlled conditions, for periods of 12.0 and 3.0 seconds. Charred specimens are thereafter subjected to controlled tearing tests, using tabulated weights, to determine the average tear length as representing the char length of the fabric. In addition, samples which are wholly consumed by the flame are rated (B) and samples which do not burn are rated (NB). For comparison pusposes, it should be noted that untreated samples of the fabrics used in the examples of this case would be consumed for this test.

In all the examples of the application, the following general procedure was used except when otherwise specifically noted. Padding was done on a standard two roll laboratory padder at a gauge pressure of about 60 pounds per square inch in all cases. Drying and curing during processing were done with a standard laboratory textile circulating air oven. Washing ahd drying was done in a standard, home, top loading, automatic washer and dryer.

The following examples are set forth for puspo:es of illustration only and are not to be construed as limitations of the present invention except as set forth in the appended claims. All parts and percentages are by weight unless otherwise specified.

EXAMPLE I

A 1 liter flask, equipped with a mechanical stirrer, thermometer and reflux condenser, was charged with 171.2g (1.0 mole) of p-toluenesulfonamide, 30g. (1.0 mole) of paraformaldehyde and 200 ml. methanol. Sodium methoxide was added to the solution to obtain a pH of 10 and thereafter the solution was refluxed for 48 hours and cooled. 150g. (1.2 mole) of trimethyl phosphite was added to the cooled reaction mixture (N-hydroxymethyl-p-toluene sulfonamide) and, after an induction period of about 5 minutes, a vigorous exotherm ensued causing the reaction mixture to reflux. After the exotherm had subsided the reaction solution was heated at reflux for 15 hours and then cooled to room temperature. On standing, colorless crystals separated from the solution. The crystals were filtered off the solution and dried resulting in a yield of 179g. A further concentration of the mother liquor, after filtration, yielded a further 40g. of crystalline material. Total yield of product was 219g. of a colorless crystalline solid analyzed as essentially pure N-dimethyl phosphonomethyl-p-toluene sulfonamide.

Elemental Analyses: Calculated: C,41.0; H,5.5; N,4.8; P,10.6. Found: C,40.6; H,5.7; N, 4.6; P,10.5.

EXAMPLE II

Following the procedure described in Example I. Sodium methoxide was added to a solution of 95.1g (1.0 mole) of methanesulfonamide, 30g. (1.0 mole) pf paraformaldehyde and 300 ml. of methanol until a pH of 10 was obtained. The reaction mixture was refluxed for 15 hours then cooled and 124g. (1.0 mole) of trimethyl phosphite added. Refluxing was then continued for a further 15 hours. The reaction solution was stripped of methanol at 70° under a vacuum of 20 mm. mercury to yield 216g. of a colorless liquid product. Analyzed as essentially pure N-dimethyl phos- phonomethyl methyl sulfonamide.

Elemental Analyses: Calculated: C,22.1; H,5.5; N,6.5; P,14.3. Found: C,21.8; H,6.0; N,5.9; P,14.5.

EXAMPLE III

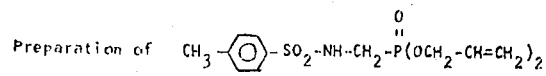

N-Hydroxymethyl-p-toluene sulfonamide prepared as in Example I. Triallyl phosphite, 40.2g. (0.2 mole) was added to the hydroxymethyl compound, 20.1g. (0.1 mole), in a round bottomed flask, and warmed to and maintained at about 125°C for 3 hours. The mixture was then stripped at about 0.5 mm Hg and about 100°C to remove all volatile material. The product was 34.5g. of a colorless liquid whose structure was confirmed by infrared and nuclear magnetic resonance spectroscopy and elemental analysis to be that of the claimed product.

EXAMPLE IV

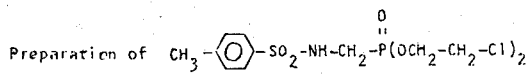

Preparation of $CH_3-\langle O \rangle-SO_2-NH-CH_2-P(OCH_2-CH_2-Cl)_2$

N-Hydroxymethyl-p-toluene sulfonamide was prepared as in Example I. The hydroxymethyl derivative, 20.1g. (0.1 mole) was then added to 27g. (0.1 mole) of tris-2-chloroethyl phosphite and warmed to 120°C. The reaction mixture was held at 120°C for two hours and then stripped at 100°C and 0.5 mm Hg to give the desired product. The product, a light brown solid, was obtained in quantitative yield and elemental and spectroscopic analysis showed it to be essentially pure.

EXAMPLE V

Preparation of $CH_3-SO_2-NH-CH_2-\overset{O}{\underset{\|}{P}}-\left(O-\langle O \rangle\right)_2$ N-Hydroxymethyl methane sulfonamide was prepared as in Example 2 above. The hydroxymethyl derivative, 12.5g (0.1 mole) was added to 31.0g of triphenyl phosphite (0.1 mole), in a round bottomed flask, and heated at about 130°C for about 5 hours. At the end of this time the reaction mixture was stripped, at about 2 mm Hg and about 120°C, to remove phenol and other volatiles. A viscous yellow liquid, was obtained in quantitative yield, with elemental analyses, infrared and nuclear magnetic spectroscopy confirming the structure as the desired product.

EXAMPLE VI

A padding solution was prepared by mixing N-dimethylphosphono-methyl-p-toluenesulfonamide, (40.0g) with 60.0g of 40% formalin solution at a pH of 9–10 and stirring overnight. The pH was adjusted to 7.0 with hydrochloric acid and 23g. of a 50% solution of a methylolated melamine and 5g of ammonium chloride added.

6.0 oz. sq. yd. wool textile material was padded through the above mixture and the excess squeezed out by means of a two roll laboratory padder at 60 lb. gauge pressure to a wet pickup of about 130%. The textile material was dried at about 250°F for about two minutes, and cured at about 350°F for about four minutes in a circulating air oven. Samples of the textile material was then washed in a standard automatic home washer, for one or five wash cycles, using Tide as the detergent, and thereafter, subjecting to AATCC test method 34–1969 to determine flammability, the results therefore indicated in Table I.

EXAMPLE VII

A padding solution, using dimethyl phosphonomethyl methane sulfonamide, was preapared as in Example VI. Cotton cloth 5.0 oz. sq. yd. was treated with the above padding solution in accordance with Example VI with results as indicated in Table I.

EXAMPLE VIII 6.0 oz. sq. yd. wool textile material was treated and tested by the padding solution and procedure of Example VII. AATCC test method 34–1969 results are as indicated in Table I.

EXAMPLE IX

A padding solution, using N-diallylphosphonomethyl-p-toluenesulfonamide, was prepared as in Example VI. Rayon sample fiber material was treated with the above padding solution in accordance with Example VI with the exception that drying and curing was at 250°F for about 3 minutes and 350°F for about seven minutes respectively. Testing of the rayon sample fibers was accomplished by holding samples thereof in a controlled burner flame for two seconds then removing and observing for self-extinguishment (SE). The treated rayon fibers were self-extinguishing upon removal while untreated fibers were consumed.

TABLE I

| Example | Substrate | Compound | Percent Wet pickup | Percent Add-on | Initial OI | Flammability Initial | Flammability Finishes |
|---|---|---|---|---|---|---|---|
| VI | Wool | $CH_3-\langle O \rangle-SO_2-NH-CH_2-\overset{O}{\underset{\|}{P}}(OCH_3)_2$ | | | 24 | 3.7 | 5.1 |
| VII | Cotton | $CH_3-SO_2-CH_2-\overset{O}{\underset{\|}{P}}(OCH_3)_2$ | | | 22 | 5.5 | 6.1 |
| IX | Rayon | $CH_3-\langle O \rangle-SO_2-NH-CH_2-\overset{O}{\underset{\|}{P}}(OCH_2CH=CH_2)_2$ | 100 | 38 | 23 | SE | SE |
| VIII | Wool | $CH_3-SO_2-CH_2-\overset{O}{\underset{\|}{P}}(OCH_3)_2$ | 130 | 77 | 28 | 3.2 | 3.2 |

EXAMPLE X 30 parts of N-dimethyl phosphonomethyl-p-toluene sulfonamide was mixed with 70 parts of polypropylene and dry blended for about 5 minutes. This composition was then heated to a melt and mixed in the molten state for about 15 minutes. The composition was allowed to cool and solidify after which it was cut into small pieces. These small composition pieces were then slowly placed into a 9 mm glass tube, immersed in a hot metal salt bath, maintained at a temperature above the melting point of the composition. A metal rod was then placed in the tube with a weight attached thereto and the tube was cooled to solidify the composition. The composition was then removed from the tube and tested by ASTM test methods D2863-70 and D635-68. The results of the testing are tabulated in Table II.

EXAMPLES XI–XIX

Using the same procedure as Example X, samples were prepared using different sulfonamidomethyl phosphonate in various plastics. The results of flammability testing thereon is indicated in Table II.

TABLE II

| Example | Plastic | Compound | Percent Add-on | OI | D-635 |
|---|---|---|---|---|---|
| X | Polypropylene |  | 30 | 19 | NB |
| XI | Polystyrene | $CH_3-SO_2-NH-CH_2-\overset{O}{\underset{\parallel}{P}}(OCH_3)_2$ | 30 | 19.7 | NB |
| XII | ABS |  | 30 | 20.1 | NB |
| XIII | Nylon | $CH_3-SO_2-NH-CH_2-\overset{O}{\underset{\parallel}{P}}(OCH_3)_2$ | 30 | 23 | NB |
| XIV | Epoxy | Do. | 30 | | NB |
| XV | SBR | Do. | 30 | | NB |
| XVI | Polyethylene terephthalate | | 30 | | NB |
| XVII | Nylon |  | 30 | 23 | NB |
| XVIII | Polypropylene | $CH_3-SO_2-NH-CH_2-\overset{O}{\underset{\parallel}{P}}(O\phi)_2$ | 30 | 22.7 | NB |
| XIX | ABS |  | 30 | 24.2 | NB |

We claim:

1. An article comprising a textile selected from the group consisting of cellulosic fibers, proteinaceous fibers and blends thereof and a flame retardant amount of a compound of the formula $$RSO_2NHCH_2\overset{O}{\underset{\parallel}{P}}(OR')_2$$

wherein R is selected from the group consisting of lower alkyl of 1–6 carbon atoms, phenyl and alkyl substituted phenyl, and R' is selected from the group consisting of phenyl, lower alkenyl and halogen substituted and unsubstituted lower alkyl of 1–6 carbon atoms.

2. The article of claim 1 wherein said compound is $$CH_3-SO_2-NH-CH_2-\overset{O}{\underset{\parallel}{P}}(OCH_3)_2.$$

3. The article of claim 1 wherein said compound is $$CH_3-CH_2-SO_2-NH-CH_2-\overset{O}{\underset{\parallel}{P}}(OCH_3)_2.$$

4. The article of claim 1 wherein said compound is $$CH_3-CH_2-CH_2-CH_2-SO_2-NH-CH_2-\overset{O}{\underset{\parallel}{P}}(OCH_3)_2.$$

5. The article of claim 1 wherein said compound is $$CH_3-SO_2-NH-CH_2-\overset{O}{\underset{\parallel}{P}}(OCH_2-CH_3)_2.$$

6. The article of claim 1 wherein said compound is $$CH_3-SO_2-NH-CH_2-\overset{O}{\underset{\parallel}{P}}(OCH_2-CH-Br-CH_2-Br)_2.$$

7. The article of claim 1 wherein said compound is

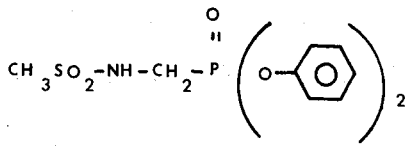

8. The article of claim 1 wherein said compound is

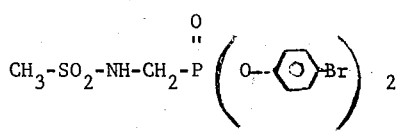

9. The article of claim 1 wherein said compound is

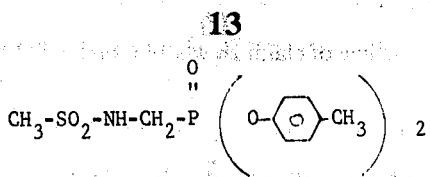

10. The article of claim 1 wherein said compound is

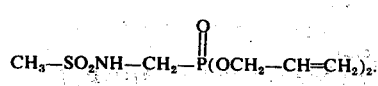

11. The article of claim 1 wherein said compound is

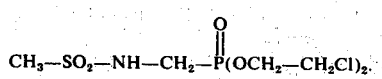

12. The article of claim 1 wherein said compound is

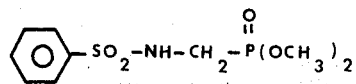

13. The article of claim 1 wherein said compound is

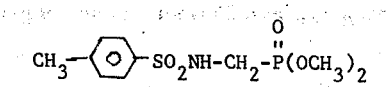

14. The article of claim 1 wherein said compound is

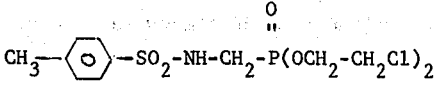

15. The article of claim 1 wherein said compound is

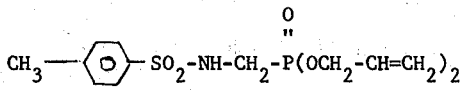

16. The article of claim 1 wherein said compound is

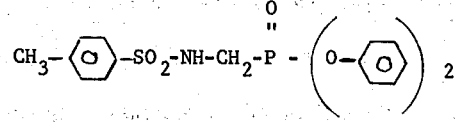

17. The article of claim 1 wherein said compound is

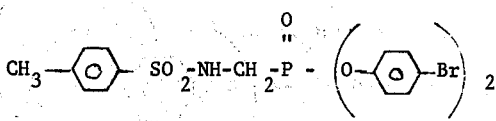

18. The article of claim 1 wherein said compound is

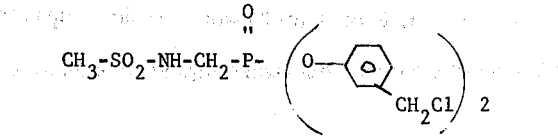

19. The article of claim 1 wherein said compound is

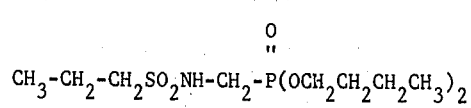

20. The article of claim 1 wherein said compound is

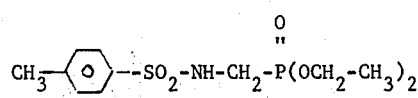

21. The article of claim 1 wherein said compound is

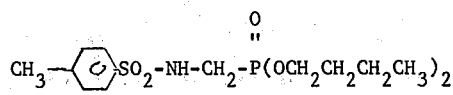

22. The article of claim 1 wherein said compound is

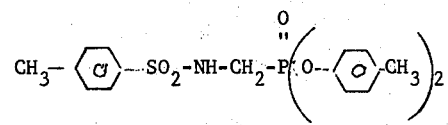

23. The article of claim 1 wherein said compound is

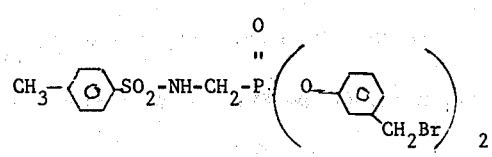

24. The article of claim 1 wherein said compound is

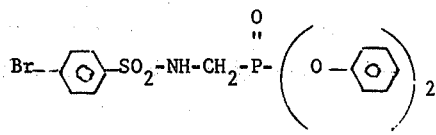

25. The article of claim 1 wherein said compound is

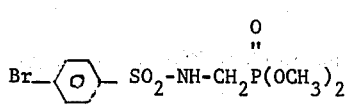

26. An article comprising a resin compound and a flame retardant amount of a compound of the formula

wherein R is selected from the group consisting of lower alkyl of 1–6 carbon atoms, phenyl and alkyl substituted phenyl, and R' is selected from the group consisting of phenyl, lower alkenyl and halogen substituted and unsubstituted lower alkyl of 1–6 carbon atoms.

27. The article of claim 26 wherein said compound is

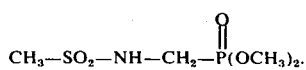

28. The article of claim 26 wherein said compound is

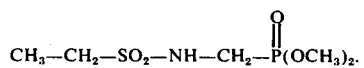

29. The article of claim 26 wherein said compound is

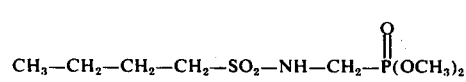

30. The article of claim 26 wherein said compound is

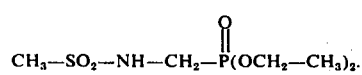

31. The article of claim 26 wherein said compound is

32. The article of claim 26 wherein said compound is

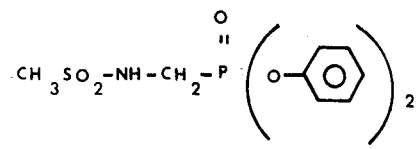

33. The article of claim 26 wherein said compound is

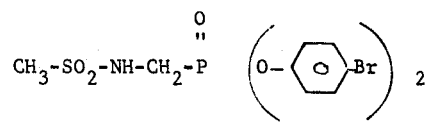

34. The article of claim 26 wherein said compound is

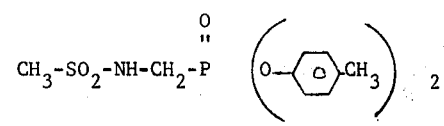

35. The article of claim 26 wherein said compound is

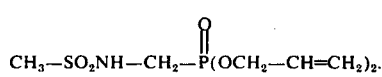

36. The article of claim 26 wherein said compound is

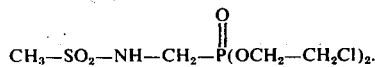

37. The article of claim 26 wherein said compound is

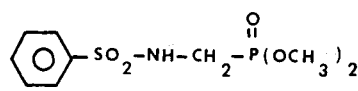

38. The article of claim 26 wherein said compound is

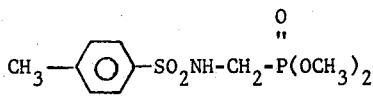

39. The article of claim 26 wherein said compound is

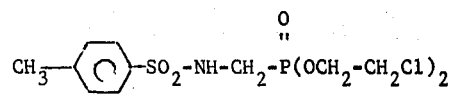

40. The article of claim 26 wherein said compound is

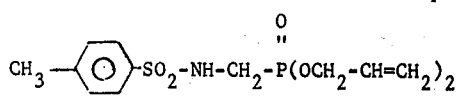

41. An article of claim 26 wherein said compound is

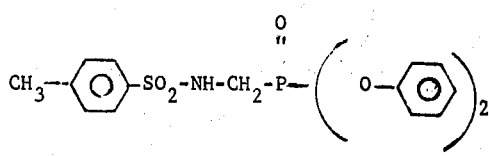

42. An article of claim 26 wherein said compound is

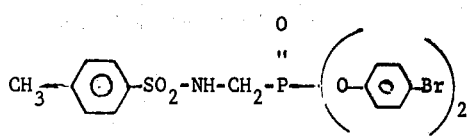

43. The article of claim 26 wherein said compound is

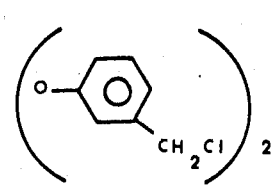

44. The article of claim 26 wherein said compound is

CH₃—CH₂—CH₂SO₂NH—CH₂—P(O)(OCH₂CH₂CH₂CH₃)₂.

45. The article of claim 26 wherein said compound is

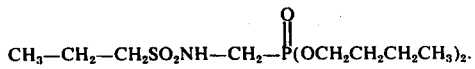

46. The article of claim 26 wherein said compound is

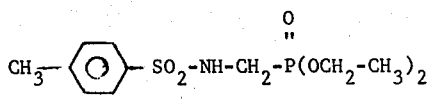

47. The article of claim 26 wherein said compound is

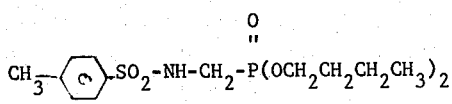

48. An article of claim 26 wherein said compound is

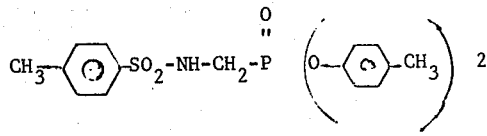

49. An article of claim 26 wherein said compound is

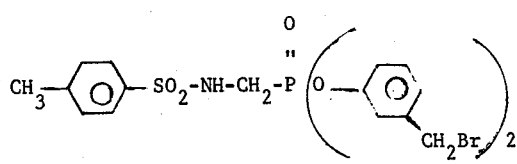

50. An article of claim 26 wherein said compound is

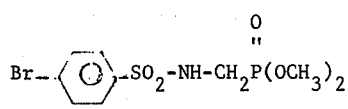

51. A process for rendering textiles flame retardant which comprises applying to the textile a flame retardant amount of a compound of the formula

wherein R is selected from the group consisting of lower alkyl of 1–6 carbon atoms, phenyl and alkyl substituted phenyl, and R' is selected from the group consisting of phenyl, lower alkenyl and halogen substituted and unsubstituted lower alkyl of 1–6 carbon atoms.

52. The process of claim 51 wherein said textile is selected from the group consisting of cellulosic fibers, proteinaceous fibers and blends thereof.

53. A process for rendering resin compositions flame retardant which comprises applying to the resin composition a flame retardant amount of a compound of the formula

wherein R is selected from the group consisting of lower alkyl of 1–6 carbon atoms, phenyl and alkyl substituted phenyl, and R' is selected from the group consisting of phenyl, lower alkenyl and halogen substituted and unsubstituted lower alkyl of 1–6 carbon atoms.

54. The process of claim 53 wherein the resin composition is a thermoplastic resin composition.

55. The process of claim 53 wherein the resin composition is a thermosetting resin composition.

56. The process of claim 53 wherein the resin composition is an elastomeric resin composition.

* * * * *